(12) United States Patent
Snyder

(10) Patent No.: US 8,481,694 B2
(45) Date of Patent: Jul. 9, 2013

(54) PURIFICATION OF IMMUNOCONJUGATES

(75) Inventor: Mark Snyder, Oakland, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 414 days.

(21) Appl. No.: 12/769,460

(22) Filed: Apr. 28, 2010

(65) Prior Publication Data

US 2010/0280228 A1  Nov. 4, 2010

Related U.S. Application Data

(60) Provisional application No. 61/173,896, filed on Apr. 29, 2009.

(51) Int. Cl.
*A23J 1/00* (2006.01)
(52) U.S. Cl.
USPC .......................... 530/412; 530/416; 530/417
(58) Field of Classification Search
None
See application file for complete search history.

(56) References Cited

U.S. PATENT DOCUMENTS

| 2005/0031627 | A1* | 2/2005 | Mazzola et al. | 424/178.1 |
| 2006/0160998 | A1 | 7/2006 | Suk | |
| 2007/0048314 | A1 | 3/2007 | Dai et al. | |
| 2009/0220492 | A1* | 9/2009 | Basey et al. | 424/130.1 |
| 2011/0263823 | A1* | 10/2011 | Gagnon | 530/350 |

FOREIGN PATENT DOCUMENTS

| WO | 03/057163 A2 | 7/2003 |
| WO | 2007/024536 A2 | 3/2007 |
| WO | 2009/017491 A1 | 2/2009 |

OTHER PUBLICATIONS

Freitag et al. "Isolation and purification of recombinant proteins, antibodies and plasmid DNA with hydroxyapatite chromatography" Biotechnol. J. 2012, 7, 90-102.*
Gagnon, Pete et al.; "A Ceramic Hydroxyapatite-Based Purification Platform: Simultaneous Removal of Leached Protein A, Aggregates, DNA, and Endotoxins from MAbs"; 2006, *BioProcess International*, pp. 50-60.
CHT™ Ceramic Hydroxyapatite—A New Dimension in Chromatography of Biological Molecules; 1996, *Bio Rad Tech Note 2156*, 4 pages.
CHT® Ceramic Hydroxyapatite Instruction Manual, *Bio Rad*, 15 pages, date unknown.
Supplementary European Search Report from EP 10770248.2 mailed Sep. 27, 2012 (2 pages).
Schubert et al.; "Comparison of ceramic hydroxyl- and fluoroapatite versus protein A/G-based resin in the isolation of a recombinant human antibody from cell culture supernatant", *Journal of Chromatography A;* 1142:106-113 (2007).

* cited by examiner

*Primary Examiner* — Daniel E Kolker
*Assistant Examiner* — James Rogers
(74) *Attorney, Agent, or Firm* — Kilpatrick Townsend & Stockton LLP

(57) ABSTRACT

The present invention provides methods of purifying immunoconjugates.

11 Claims, 18 Drawing Sheets

PURIFICATION OF IMMUNOCONJUGATES

CROSS-REFERENCE TO RELATED PATENT APPLICATIONS

The present patent application claims benefit of priority to U.S. Provisional Patent Application No. 61/173,896, filed Apr. 29, 2009, which is incorporated by reference for all purposes.

BACKGROUND OF THE INVENTION

Immunoconjugates of various sorts have been described and used in the scientific and medical literature. For example, conjugates of antibodies and fluorescent or other types of detectable labels have a wide variety of uses for diagnostic and other research areas. Conjugates of antibodies and toxins, radioisotopes, or other biologically active compounds have a variety of therapeutic uses.

Generation of immunoconjugates can involve linking an antibody to another agent. Such reactions are not 100% efficient and thus the reaction typically results in the production of a desired immunoconjugate as well as some amount of the unconjugated components, i.e., unconjugated antibody and one or more unconjugated agents (unconjugated label, unconjugated toxin, etc.).

BRIEF SUMMARY OF THE INVENTION

The present invention provides methods of purifying an antibody-agent conjugate from unconjugated antibody and unconjugated agent. In some embodiments, the method comprises:
(a) contacting a mixture of conjugate, unconjugated antibody, and unconjugated agent to a mixed mode chromatography support under conditions to allow binding of the conjugate, unconjugated antibody, and unconjugated agent to the support;
(b) contacting the support with a buffer such that the unconjugated antibody and unconjugated agent are substantially removed from the support while at least a majority of the conjugate remains bound to the support; and then
(c) eluting the conjugate from the support, thereby purifying the antibody-agent conjugate from unconjugated antibody and unconjugated agent.

In some embodiments, the buffer in step (b) comprises an increased concentration of salt compared to the mixture of step (a). In some embodiments, the concentration of salt is between 0.5 and 4M. In some embodiments, the salt is NaCl.

In some embodiments, step (c) comprises increasing the concentration of the buffer compared to the concentration in step (b). In some embodiments, step (c) comprises reducing the salt concentration compared to the salt concentration in step (b).

In some embodiments, the pH of the mixture in step (a) is between about pH 5.5 and pH 8.5 (e.g., 5.5-8.5, 5.5-7, 5.5-6.5, 6-7, 6-8, etc.).

In some embodiments, the pH of the buffer in step (b) is between about pH 5.5. and pH 8.5 (e.g., 5.5-8.5, 5.5-7, 5.5-6.5, 6-7, 6-8, etc.).

In some embodiments, the eluting step comprises contacting the support with an elution buffer having a pH between about pH 5.5. and pH 11 (e.g., 5.5-8.5, 5.5-7, 5.5-6.5, 6-7, 6-8, etc.).

In some embodiments, the buffer is a phosphate buffer.

In some embodiments, the agent is selected from the group consisting of a label, hormone, cytotoxic agent, and a radio-isotope. In some embodiments, the label is a fluorescent label. In some embodiments, the fluorescent label is phycoerythrin.

In some embodiments, the mixed mode support comprises ceramic hydroxyapatite (CHT) or ceramic fluorapatite (CFT). In some embodiments, the CHT is selected from the group consisting of hydroxyapatite CHT Type I, 20 micron; hydroxyapatite CHT Type I, 40 micron; hydroxyapatite CHT Type I, 80 micron; hydroxyapatite CHT Type II, 20 micron; hydroxyapatite CHT Type II, 40 micron; and hydroxyapatite CHT Type II, 80 micron. In some embodiments, the CFT is selected from the group consisting of CFT Type I, 40 micron and CFT Type II, 40 micron.

The present invention also provides a mixture of conjugate, unconjugated antibody, and unconjugated agent in contact with a mixed mode chromatography support. In some embodiments, the mixture is contacted under conditions to allow binding of the conjugate, unconjugated antibody, and unconjugated agent to the support.

In some embodiments, the agent is selected from the group consisting of a label, hormone, cytotoxic agent, and a radio-isotope. In some embodiments, the label is a fluorescent label. In some embodiments, the fluorescent label is phycoerythrin.

In some embodiments, the mixed mode support comprises ceramic hydroxyapatite (CHT) or ceramic fluorapatite (CFT). In some embodiments, the CHT is selected from the group consisting of hydroxyapatite CHT Type I, 20 micron; hydroxyapatite CHT Type I, 40 micron; hydroxyapatite CHT Type I, 80 micron; hydroxyapatite CHT Type II, 20 micron; hydroxyapatite CHT Type II, 40 micron; and hydroxyapatite CHT Type II, 80 micron. In some embodiments, the CFT is selected from the group consisting of CFT Type I, 40 micron and CFT Type II, 40 micron.

Definitions

"Antibody" refers to an immunoglobulin, composite, or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')2, Fv, scFv, Fd, dAb, Fc and other compositions, whether or not they retain antigen-binding function.

"Mixed mode chromatography support" refers to a chromatographic solid phase that substantially involves a combination of two or more chemical mechanisms. Examples of chemical mechanisms that can be combined in mixed mode supports include but are not limited to cation exchange, anion exchange, hydrophobic interaction, hydrophilic interaction, hydrogen bonding, pi-pi bonding, and metal affinity. The solid phase can be a porous particle, nonporous particle, membrane, or monolith. Mixed mode chromatography is sometimes referred to as "multimodal" chromatography.

"Hydroxyapatite" refers to a mixed mode support comprising an insoluble hydroxylated mineral of calcium phosphate with the structural formula $Ca_{10}(PO_4)_6(OH)_2$. Its dominant modes of interaction are phosphoryl cation exchange and calcium metal affinity. Hydroxapatite is commercially available in various forms, including but not limited to ceramic, crystalline and composite forms. Composite forms contain hydroxyapatite microcrystals entrapped within the pores of agarose or other beads.

"Fluorapatite" refers to a mixed mode support comprising an insoluble fluoridated mineral of calcium phosphate with the structural formula $Ca_{10}(PO_4)_6F_2$. Its dominant modes of interaction are phosphoryl cation exchange and calcium metal affinity. Fluorapatite is commercially available in various forms, including but not limited to ceramic and crystalline composite forms.

"Ceramic" hydroxyapatite (CHT) or "ceramic" fluorapatite (CFT) refer to forms of the respective minerals in which nanocrystals are agglomerated into particles and fused at high temperature to create stable ceramic microspheres suitable for chromatography applications. Commercial examples of ceramic hydroxyapatite include, but are not limited to CHT Type I and CHT Type II. Commercial examples of fluorapatite include, but are not limited to CFT Type I and CFT Type II. Unless specified, CHT and CFT refer to roughly spherical particles of any average diameter, including but not limited to about 10, 20, 40, and 80 microns. The choice of hydroxyapatite or fluorapatite, the type, and average particle diameter can be determined by the skilled artisan.

DETAILED DESCRIPTION

I. Introduction

Figure 1:
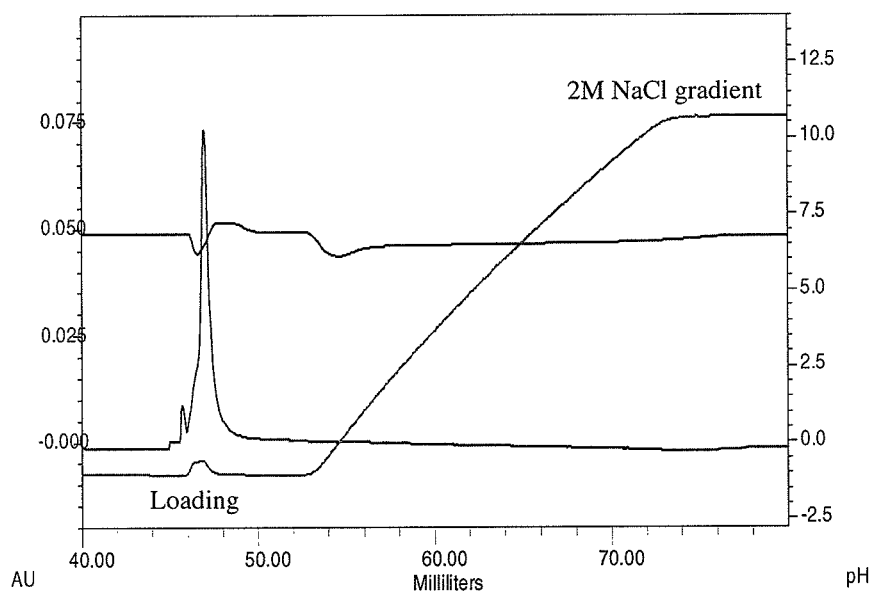
FIG. 1. CFT purification of the purified GAH-PE. Equilibration buffer: 10 mM $NaPO_4$, pH 7. Elution buffer: equilibration buffer plus 2 M NaCl. Gradient: 0 to 100% B over 20 column volumes.

The present invention relates in part to the discovery that immunoconjugates can be purified on mixed mode supports in a process by which the immunoconjugates and unconjugated reactants are bound to the support, the unconjugated reactants are then washed from the support, and subsequently the immunoconjugate is eluted from the support, thereby purifying the immunoconjugate from the unconjugated reactants.

II. Immunoconjugates

It is believed that any immunoconjugate, i.e., one or more antibody, or fragment thereof, covalently linked to another agent, can be purified by the methods of the invention.

A. Antibodies

Any antibody preparation can be used in the present invention, including unpurified or partially purified antibodies from natural, synthetic, or recombinant sources. Unpurified antibody preparations can come from various sources including, but not limited to, plasma, serum, ascites, milk, plant extracts, bacterial lysates, yeast lysates, or conditioned cell culture media. Partially purified preparations can come from unpurified preparations that have been processed by at least one chromatography, precipitation, other fractionation step, or any combination of the foregoing. In some embodiments, the antibodies have, or have not, been purified by protein A affinity prior to purification as described herein.

The antibodies, or fragments thereof, can be derived from any antibody-producing animal, including but not limited to, human, mouse, goat, rabbit, pig, bovine, and rat. The antibodies can be monoclonal or polyclonal. In some embodiments, the antibodies are single-chained antibodies or chimeric antibodies (including but not limited to humanized antibodies).

The antibody can target essentially any epitope as desired. In some cases, the antibody specifically recognizes a target cell antigen, such as a tumor cell. In some embodiments, the antibody recognizes an antibody from a different species (e.g., for use in a diagnostic assay).

B. Agents/Conjugation Partners

A wide variety of agents can be linked to antibodies. Agents can include proteins (e.g., biologically active proteins, therapeutic proteins, hormones, cytotoxic agents, toxic proteins, detectable proteins, etc.), nucleic acids, small molecules (e.g., small molecule therapeutics, diagnostics, e.g., labels, or toxins), photosensitizers (including but not limited to porphyrins and hydroporphyrins), and radioisotopes. Essentially any agent to be targeted by an antibody can be conjugated to an antibody.

A "cytotoxic agent," as used herein, refers to any compound that results in the death of a cell, induces cell death, or decreases cell viability. Suitable cytotoxic agents include, but are not limited to, ricin A chain, maytansinoids and maytansinoid analogs, taxoids, CC-1065 and CC-1065 analogs, and dolastatin and dolastatin analogs. Maytansinoids are compounds that inhibit microtubule formation and are highly toxic to mammalian cells. Examples of suitable maytansinol analogues include those having a modified aromatic ring and those having modifications at other positions. Such maytansinoids are described in, for example, U.S. Pat. Nos. 4,256,746, 4,294,757, 4,307,016, 4,313,946, 4,315,929, 4,322,348, 4,331,598, 4,361,650, 4,362,663, 4,364,866, 4,424,219, 4,371,533, 4,450,254, 5,475,092, 5,585,499, 5,846,545, and 6,333,410.

In some embodiments, the agent is a detectable label. In one aspect, antibodies of the invention may be conjugated with any label moiety through a reactive moiety, an activated moiety, or a reactive cysteine thiol group (Singh et al (2002) *Anal. Biochem.* 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The attached label may function to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or forming ionic complexes.

Numerous labels are available which can be generally grouped into the following categories:

Radioisotopes (radionuclides), such as $^3$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. Radioisotope labelled antibodies are useful, for example, in targeted imaging. The antibody can be labeled with ligand reagents that bind, chelate or otherwise complex a radioisotope metal. See, e.g., *Current Protocols in Immunology*, Volumes 1 and 2, Coligen et al, Ed. Wiley-Interscience, New York, N.Y., Pubs. (1991). Chelating ligands which may complex a metal ion include DOTA, DOTP, DOTMA, DTPA and TETA (Macrocyclics, Dallas, Tex.).

Additional labels include, e.g., fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. Fluorescent dyes and fluorescent label reagents include those which are commercially available from Invitrogen/Molecular Probes (Eugene, Oreg.) and Pierce Biotechnology, Inc. (Rockford, Ill.).

Additional labels include can also include, e.g., various enzyme-substrate labels. In some embodiments, the enzyme catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in, e.g., O'Sullivan et al (1981) "Methods for the Preparation of Enzyme-Antibody Conjugates for use in Enzyme Immunoassay", in Methods in Enzym. (ed J. Langone & H. Van Vunakis), Academic Press, New York, 73:147-166.

C. Linkers

A wide variety of linker technologies are known and can be used to link an antibody to an agent as described herein to form an immunoconjugate. For example, any suitable bifunctional crosslinking reagent can be used in connection with the invention, so long as the linker reagent provides for retention of the targeting characteristics of the antibody, and optionally does not interfere with activity of the agent linked to the antibody. In some embodiments, the linker molecule joins the drug to the antibody through chemical bonds (as described above), such that the drug and the antibody are chemically coupled (e.g., covalently bonded) to each other. In some embodiments, the linking reagent is a cleavable linker. Examples of suitable cleavable linkers include disulfide linkers, acid labile linkers, photolabile linkers, peptidase labile linkers, and esterase labile linkers. Disulfide containing linkers are linkers cleavable through disulfide exchange, which can occur under physiological conditions. Acid labile linkers are linkers cleavable at acid pH. For example, certain intracellular compartments, such as endosomes and lysosomes, have an acidic pH (pH 4-5), and provide conditions suitable to cleave acid labile linkers. Photo labile linkers are useful at the body surface and in many body cavities that are accessible to light. Furthermore, infrared light can penetrate tissue. Peptidase labile linkers can be used to cleave certain peptides inside or outside cells (see e.g., Trouet et al., *Proc. Natl. Acad. Sci. USA*, 79: 626-629 (1982), and Umemoto et al., *Int. J. Cancer*, 43: 677-684 (1989)).

In some embodiments, the agent is linked to an antibody through a disulfide bond. The linker molecule comprises a reactive chemical group that can react with the antibody. Exemplary reactive chemical groups for reaction with the antibody are N-succinimidyl esters and N-sulfosuccinimidyl esters. Additionally in some embodiments the linker molecule comprises a reactive chemical group, e.g., a dithiopyridyl group, that can react with the drug to form a disulfide bond. In some embodiments, linker molecules include, for example, N-succinimidyl 3-(2-pyridyldithio)propionate (SPDP) (see, e.g., Carlsson et al., *Biochem. J,* 173: 723-737 (1978)), N-succinimidyl 4-(2-pyridyldithio)butanoate (SPDB) (see, e.g., U.S. Pat. No. 4,563,304), and N-succinimidyl 4-(2-pyridyldithio)pentanoate (SPP) (see, e.g., CAS Registry number 341498-08-6).

A non-cleavable linker also can be used to generate the immunoconjugate. A non-cleavable linker is any chemical moiety that is capable of linking an agent to an antibody via a covalent bond. Thus, in some embodiments, non-cleavable linkers are substantially resistant to acid-induced cleavage, light-induced cleavage, peptidase-induced cleavage, esterase-induced cleavage, and disulfide bond cleavage, at conditions under which the drug or the antibody remains active.

Examples of non-cleavable linkers include linkers having an N-succinimidyl ester or N-sulfosuccinimidyl ester moiety for reaction with the cell-binding agent, as well as a maleimido- or haloacetyl-based moiety for reaction with the drug. Crosslinking reagents comprising a maleimido-based moiety include N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), .gamma.-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

Other crosslinking reagents lacking a sulfur atom that form non-cleavable linkers can also be used in the inventive method. Such linkers can be derived, for example, from dicarboxylic acid based moieties. Exemplary non-cleavable linkers are described in detail in U.S. Patent Application Publication No. 2005-0169933 A1.

In some embodiments, hydrazide, maleimide or amide chemistry is used to link the agent and the antibody. Such chemistries are useful for linking, for example, phycoerythrin to an antibody.

III. Purification

The present invention provides for methods of purifying immunoconjugates in "bind-elute" mode such that the immunoconjugates, and unconjugated immunoconjugate components (e.g., unconjugated antibody and unconjugated agent), are bound to a mixed mode support, and subsequently eluted such that the immunoconjugate is purified from the unconjugated components. "Bind-elute mode" as it relates to the invention herein, refers to an operational approach to chromatography in which the buffer conditions are established so that both a target protein (e.g., immunoconjugate) and undesired contaminants (e.g., unconjugated components) bind to the mixed mode chromatography support. Fractionation of immunoconjugate from the other components is achieved subsequently by changing the conditions such the components and the immunoconjugate are eluted separately from the support.

A. Adsorption to Solid Support

According to the invention, a mixture comprising the immunoconjugate and unconjugated components are contacted to a mixed mode support under conditions to allow for adsorption (also referred to herein as "binding") of the immunoconjugate and unconjugated components.

In preparation for contacting the immunoconjugate mixture with the mixed mode support, optionally, the chemical environment inside the column is equilibrated. This is commonly accomplished by passing an equilibration buffer through the column to establish the appropriate pH, conductivity, and other pertinent variables. In an example not intended to limit the invention, in some embodiments, the support is equilibrated at a pH between 5.5-11, e.g., 5.5-7, e.g., 6-6.5, optionally with a phosphate buffer (e.g., NaPO$_4$), e.g., from 100-800 mM, e.g., 3-600 mM, e.g., 400-550 mM, optionally wherein the mixed mode support comprises CHT or CFT.

In some embodiments, optionally, the immunoconjugate mixture is equilibrated to conditions compatible with the column equilibration buffer before the invention can be practiced.

Not all of the immunoconjugate loaded onto the support will necessarily bind to the support. Thus, some of the immunoconjugate can be lost in the initial loading process. The binding of the immunoconjugate to the support is ideally achieved with minimal flow through of the loaded immunoconjugate. The inventors have found that one way to achieve reduced flow through of the loaded materials, and thereby increase yield when using a phosphate buffering system, is to lower the phosphate buffer concentration (e.g., to 1-50 mM, e.g., 1-20 mM or 1-10 mM) during loading. Optionally, buffer capacity can be supplemented with a second buffer. In some embodiment, the second buffer is selected from the group consisting of 2-(N-morpholino)ethanesulfonic acid (MES), 4-(2-hydroxyethyl)-1-piperazineethanesulfonic acid (HEPES), 3-(N-morpholino)propanesulfonic acid (MOPS) and other commonly referred to as "Good" buffers (Good, N. E. et al., Biochemistry, 5, 467-477 (1966)). Further, as explained in the example, one can further reduce flow through of the immunoconjugate during loading by lowering the pH, e.g., to 5.5-6.5, e.g., about 6 or about 6.5. This pH can be used with, for example, CFT.

Various mixed mode chromatography media are available commercially, any of which can be used to practice of this invention. Commercially available examples include but are not limited to ceramic hydroxyapatite (CHT) or ceramic fluorapatite (CFT), MEP-Hypercel™, Capto-MMC™, Capto-Adhere™, Capto-S™, Capto-Q™, and ABx™.

In some embodiments, the mixed-mode chromatography support exploits a combination of anion exchange and hydrophobic interaction functionalities. Examples of such supports include, but are not limited to, MEP-Hypercel™.

In some embodiments, the mixed-mode chromatography support exploits a combination of cation exchange and hydrophilic interaction functionalities. Examples of such supports include, but are not limited to, Capto-S™.

In some embodiments, the mixed-mode chromatography support exploits a combination anion exchange and hydrophilic interaction functionalities. Examples of such supports include, but are not limited to, Capto-Q™.

In some embodiments, the mixed-mode chromatography support exploits a combination of cation exchange, anion exchange, and hydrophobic interaction functionalities. Examples of such supports include, but are not limited to, ABx™.

In some embodiments, the mixed-mode chromatography support exploits a combination of anion exchange and hydrophobic interaction functionalities with potential for hydrogen bonding and pi-pi bonding. Examples of such supports include, but are not limited to, Capto-Adhere™.

In some embodiments, the mixed-mode chromatography support exploits a combination of cation exchange and hydrophobic interaction functionalities with potential for hydrogen bonding and pi-pi bonding. Examples of such supports include, but are not limited to, Capto-MMC™.

The invention may be practiced in a packed bed column, a fluidized/expanded bed column containing the mixed mode support, and/or a batch operation where the mixed mode support is mixed with the antibody preparation for a certain time.

In some embodiments, a mixed mode chromatography support is packed in a column.

The mixed mode support can be packed in a column of any dimension required to support preparative applications. Column diameter may range from less than 1 cm to more than 1 meter, and column height may range from less than 1 cm to more than 30 cm depending on the requirements of a particular application.

It will be appreciated that the present invention is not limited to the above heights and diameters. Appropriate column dimensions can be determined by the skilled artisan.

B. Washing of Unconjugated Antibodies and Agents

One or more washing steps can occur following loading to substantially remove the unconjugated components (unconjugated antibody or unconjugated agent) bound to the support. By "substantially remove" it is meant that at least 75% (optionally, at least 85%, 95%, or 95% or more) of the agents are removed from the support. Conditions are selected such that the bound immunoconjugate remains bound to the support. In some embodiments, the wash conditions do not remove at least a majority of the bound immunoconjugate. Optionally at least 50%, 65%, 75%, 85%, or 90% or more of the bound immunoconjugate remains bound during the wash step(s). Exemplary wash conditions can include, e.g., increasing the salt concentration in solution compared to the concentration of salt in the loading step. For example, one can increase the amount of NaCl, KCl, sodium borate, sodium sulfate, or other soluble salt compared to the initial binding conditions, thereby removing the unconjugated components from the support. For example, the amount of salt (including but not limited to NaCl) can be increased (as a gradient or step-wise) is increased to e.g., at least 0.75 M, e.g., 1-3 M, 0.75-1.5 M, e.g., about 2 M, optionally while the buffer concentration remains unchanged and optionally is relatively low (e.g., less than 50 mM, e.g., 5-20 mM). Optionally, in some embodiments, the pH of the wash is between 5.5-11, e.g., 5.5-8.5, e.g., 6-6.5, e.g., about 6.

As the introduction of salt in the wash step can reduce the pH, a second buffer component that is relatively unaffected by the salt can also be included in the wash step. For example, one can include MES, HEPES, MOPS or other "Good" buffers (Good, N. E. et al., Biochemistry, 5, 467-477 (1966)) in the wash to maintain an essentially constant pH while increasing the salt concentration. In some embodiments, the concentration of the second buffer is, e.g., 1-200 mM, e.g., 20-40 mM, 20-60 mM, 30-50 mM, etc.

Optionally, following the wash step, one can include a further step to reequilibrate the solution in contact with the support prior to the elution.

C. Elution

Following removal of unconjugated components, the conditions can be changed again to elute the immunoconjugate. The elution conditions can comprise, for example, increasing the concentration of ion and/or buffer, thereby competing the immunoconjugate from the support. For example, in a phosphate based buffer system, in some embodiments, the buffer concentration is raised to e.g., at least 100 mM, e.g., 100-900 mM, e.g., 200-600 mM, e.g., 300-500 mM. Optionally, the pH is maintained between pH 5.5-11, e.g., 5.5-8.5, e.g., between 6-6.5.

Optionally, further salt (e.g., such as the salt used in the washing step) is not included in the elution buffer. For example, in some embodiments, the salt concentration is lower than the salt concentration in the wash step. In some cases, the salt concentration in the immunoconjugate elution step is at least 50% lower than in the prior wash step.

In some embodiments, at least 50%, 60%, 70%, 80%, 90%, or more of the immunoconjugate bound to the support is eluted in the elution step.

The purity of the resulting conjugate will vary according to the exact conditions. In some embodiments, the immunoconjugate product is at least 80%, 90%, 95%, or 98% pure.

EXAMPLE

The following example is offered to illustrate, but not to limit the claimed invention.

An effective, scalable, CFT-based method for the purification of IgG-Phycoerythrin conjugates (designated "GAH-PE") has been developed. The CFT chromatography step is tailored to be user friendly as it eliminates the traditional gradient elution method. The combination of an effective wash and a simple phosphate step elution in this single-step process generates a high-yield pool of GAH-PE conjugates with a purity of greater than 95%. The final process can be further defined when the necessary materials for the determination of column loading capacity and other process parameters is available. The progress of the development involves three stages, the early stage development with the use of the provided purified GAH-PE, the transition stage into CFT, and the final stage focusing on the definition of the wash and elution conditions. The data show that CFT and/or CHT are useful general tools for the purification of immunoconjugates from their unconjugated precursors.

Materials and Methods

IgG-Phycoerythrin conjugates: GAH-PE in the conjugation reaction mixture containing 100 mM NaCitrate, 0.15 M NaCl, pH 6.0. Hydrazide functional groups were installed on phycoerythrin and ketones were installed on IgG, and the activate molecules were coupled at a ratio of 2:1 IgG:PE at pH 6.1 for three hours.

Purified IgG-Phycoerythrin conjugates: GAH-PE in 50 mM $NaPO_4$, 0.15 M NaCl, 0.1% NaAzide, pH 7.4.

Goat IgG ("GAH"): GAH in 100 mM $NaPO_4$, 0.15 M NaCl, pH 7.2.

Chromatography resins:
Ceramic Fluoroapatite CFT Type II (40 μm)
Ceramic Hydroxyapatite CHT Type I (40 μm)
CFT column: 0.5×5.1 cm
CHT column: 0.5×5.1 cm
High performance size exclusion chromatography (HPSEC) column: Zorbax GF450 (9.4×250 mm), P.N. 884973-902 from Agilent. Guard Column (4.6×12.5 mm), P.N. 820950-911 from Agilent.
Bio-Gel P6 spin column: Cat#732-6221 from Bio-Rad.
Chromatography system: BioLogic DuoFlow QuadTec 10 system from Bio-Rad Laboratories.

Results and Discussion

The purified GAH-PE was diluted five-fold with water to lower the phosphate concentration to 10 mM before loading on a CFT column (0.5×5.1 cm) that was initially equilibrated with 10 mM $NaPO_4$, pH 7. The GAH-PE was then eluted by a linear gradient to 2 M NaCl over 20 column volumes. As shown in FIG. 1, GAH-PE flowed through the column during the loading which was verified later by SDS-PAGE analysis (data not shown). No GAH-PE was found during the NaCl gradient elution. A pH drop from 6.9 to 6.1 was observed in the beginning of the NaCl gradient elution when the conductivity started to rise. This is probably due to the displacement of the protons on the surface of CFT into the buffer by the increasing sodium ion concentration.

Figure 2:
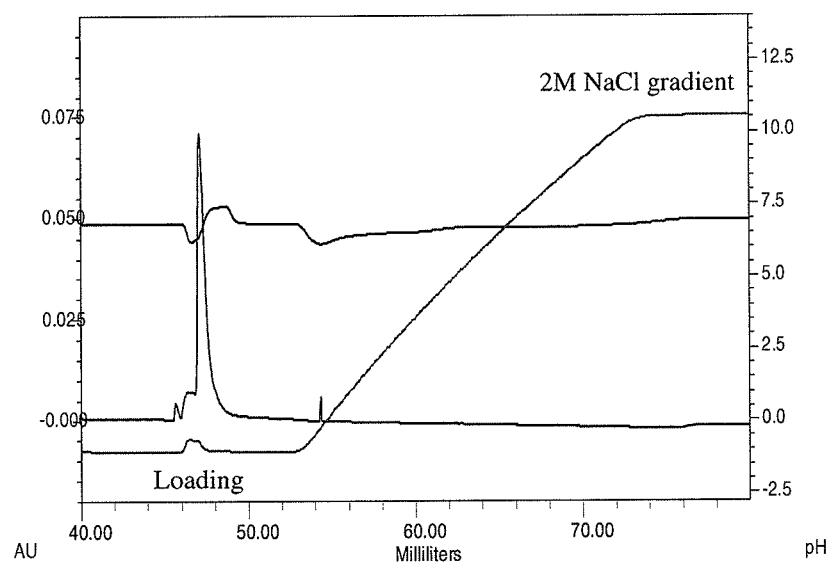
FIG. 2. CHT purification of the purified GAH-PE. Equilibration buffer: 10 mM $NaPO_4$, pH 7.

The above experiment was repeated using a CHT column (FIG. 2). Almost identical results were obtained. The pH drop was very similar from 6.8 to 6.1.

Figure 3:
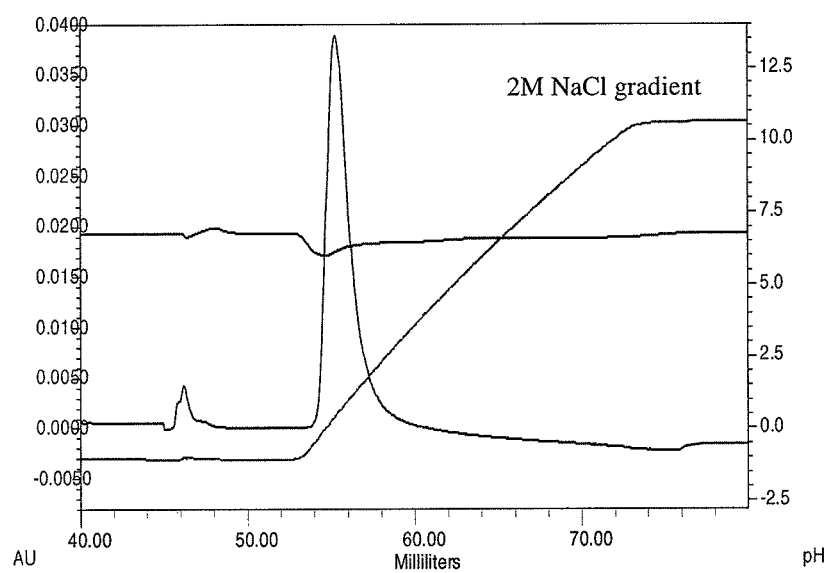
FIG. 3. CFT purification of GAH. Equilibration buffer: 10 mM $NaPO_4$, pH 7.

Goat IgG (GAH) was diluted 10-fold with water to lower the phosphate concentration to 10 mM before loading on the CFT column. It was shown in FIG. 3 that GAH was retained during the loading and eluted as a sharp peak during the NaCl gradient elution. The binding of GAH to the CFT is weak under this condition as it elutes in the early part of the gradient.

Figure 4:
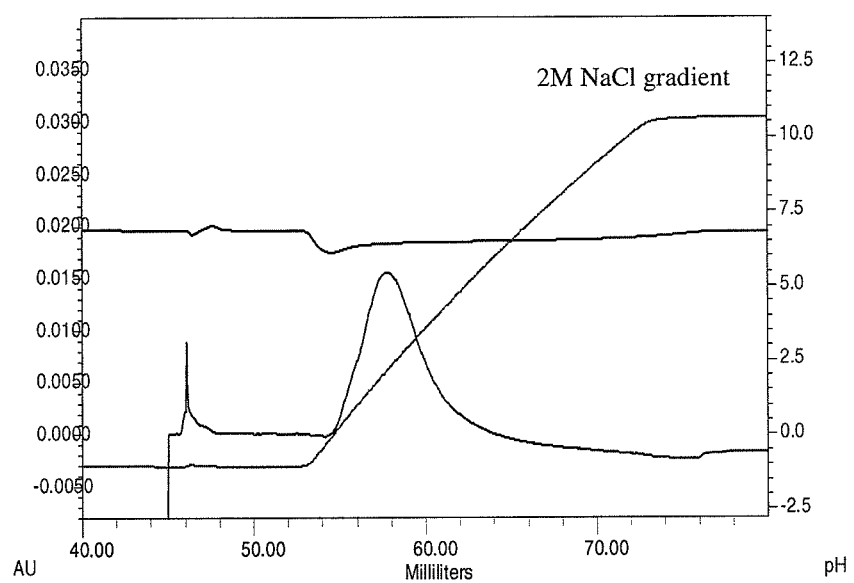
FIG. 4. CHT purification of GAH. Equilibration buffer: 10 mM $NaPO_4$, pH 7.

GAH was diluted in the same way and loaded on a CHT column (FIG. 4). GAH was retained by the column during the loading and eluted as a broad peak. This indicates that GAH has a higher binding affinity to CHT than to CFT.

The behaviors of GAH-PE and GAH on CFT and CHT indicated that GAH-PE and GAH could be separated with the GAH-PE in the loading flow-through and the retained GAH eluted by NaCl gradient.

Figure 5:
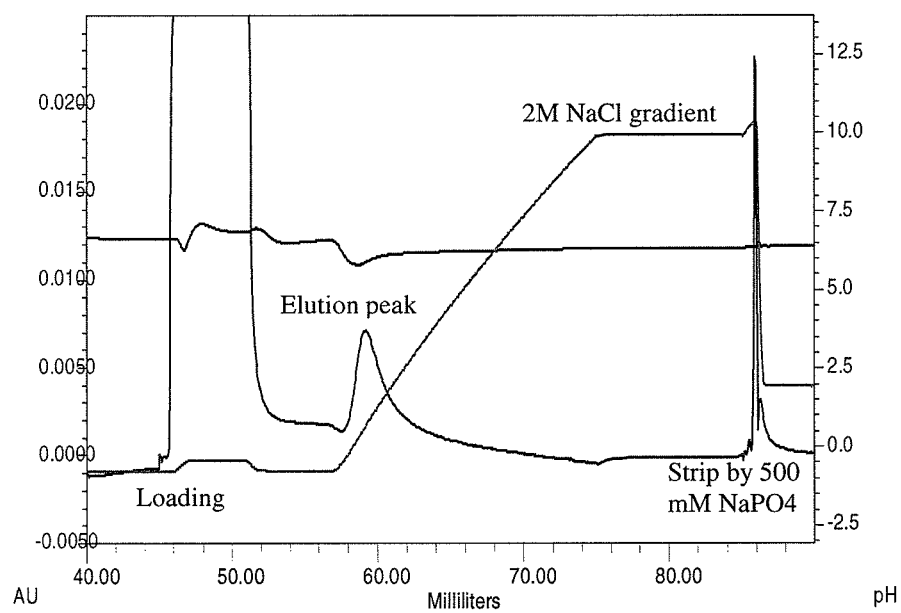
FIG. 5. CFT purification of the GAH-PE in the conjugation reaction mixture. Equilibration buffer: 10 mM $NaPO_4$, pH 7.
Figure 6:
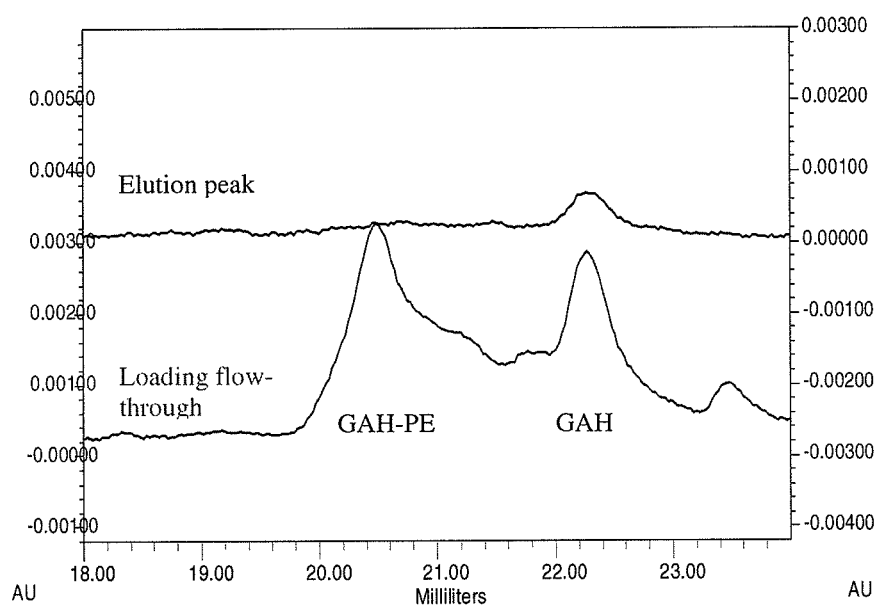
FIG. 6. HPSEC analysis of CFT flow-through peak and elution peak in FIG. 5. Running buffer: 50 mM $NaPO_4$, 1 M NaCl, 2 M urea, pH 7.

In one experiment, the conjugation reaction mixture contained 100 mM sodium citrate, which is known to be harmful to the stability of CHT and CFT and to column binding capacity. Thus, the conjugation mix was first diluted 10-fold to lower the sodium citrate concentration to 10 mM. The sodium phosphate concentration was also adjusted to 10 mM before loading on the CHT and CFT columns. The CFT chromatogram for the purification of the GAH-PE in the conjugation reaction mixture is shown in FIG. 5. There is a large peak in the loading flow-through. A relatively small peak is presented during the NaCl gradient elution. HPSEC analysis of the flow-through peak and the elution peak indicates that GAH-PE, GAH, and other contaminants flow through the column during the loading and a small amount of GAH is retained and subsequently eluted by the NaCl gradient (FIG. 6). The same results were obtained when CHT was used in the experiment (data not shown). The presence of residual sodium citrate at 10 mM along with the 10 mM sodium phosphate in the load was deemed the cause for GAH to flow through the column.

To remove the sodium citrate, the conjugation reaction mixture was exchanged into 10 mM $NaPO_4$, pH 7 using P6 spin columns before repeating the experiment. Although the binding affinity of GAH to the CFT column was improved, some amount of GAH was still found in the end of the loading flow-through (data not shown). The different behavior of the GAH from what was observed in the early stage of the development may be due to the modification of the primary amino groups on GAH by succinimidyl 4-formylbenzoate for the conjugation reaction.

Figure 7:
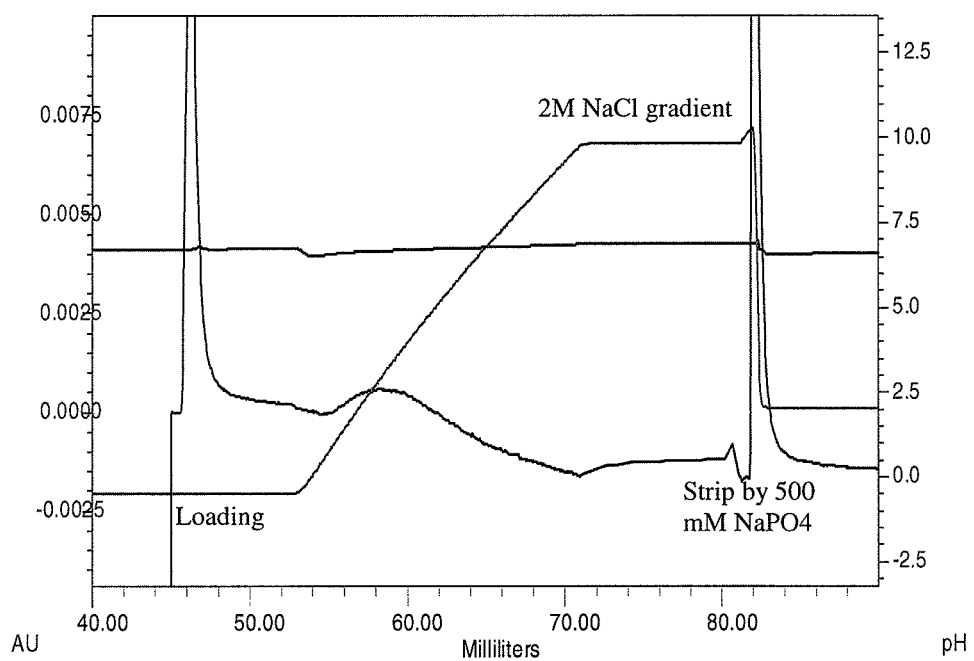
FIG. 7. CFT purification of GAH-PE in the reaction mixture exchanged into 2 mM $NaPO_4$, 50 mM MES, pH 7. Equilibration buffer: 2 mM $NaPO_4$, 50 mM MES, pH 7. Elution buffer: equilibration buffer plus 2 M NaCl. Gradient: 0 to 100%B over 20 column volumes.
Figure 8:
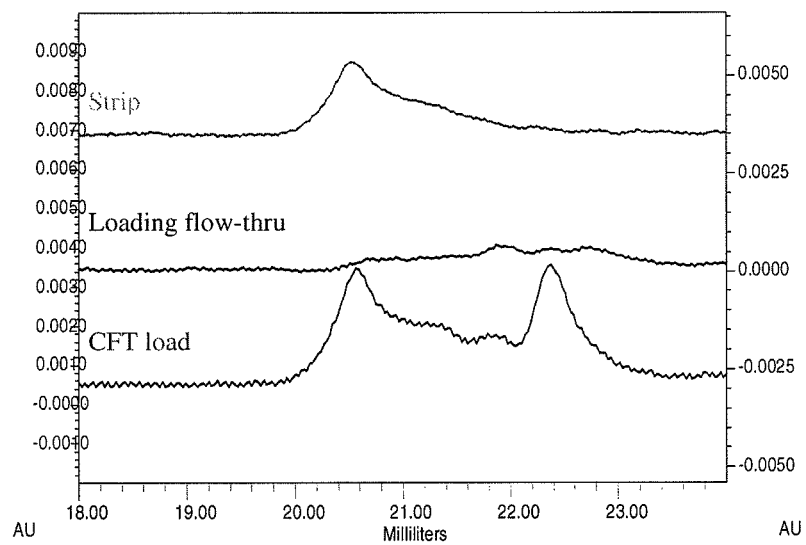
FIG. 8. HPSEC analysis of the CFT samples in FIG. 7. Running buffer: 50 mM $NaPO_4$, 1 M NaCl, 2 M urea, pH 7.

To improve the binding affinity of GAH to the CFT column, the sodium phosphate concentration was lowered to 2 mM through buffer exchange into 2 mM $NaPO_4$, 50 mM MES, pH 7. The CFT chromatogram shows that the elution peak shifts to the right and becomes broader and there is a relatively large strip peak by 500 mM $NaPO_4$ (FIG. 7). HPSEC analysis indicates that only a small amount of GAH-PE and GAH flowed through the column during the loading with the major component of the large strip peak being GAH-PE (FIG. 8). This indicates that both GAH-PE and GAH bind to the CFT column in 2 mM $NaPO_4$, 50 mM MES, pH 7 and GAH-PE has a much higher affinity to the CFT than GAH once it binds to the column.

Figure 9:
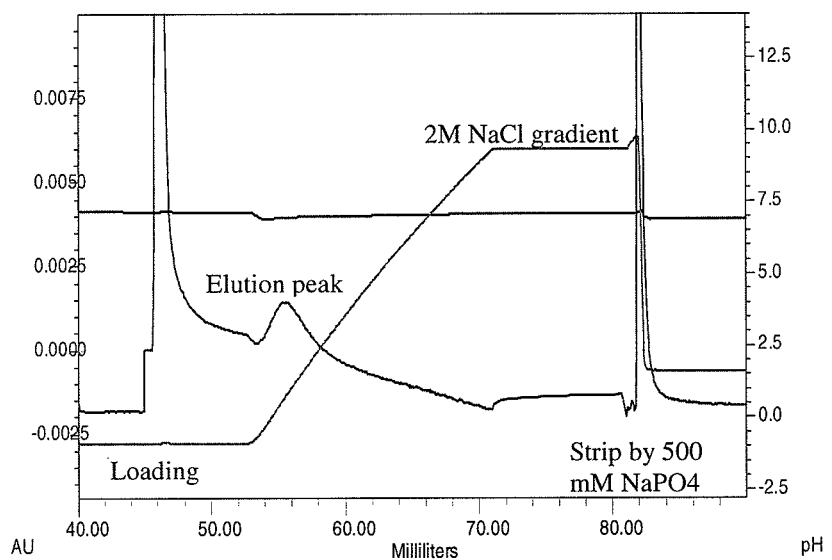
FIG. 9. CFT purification of the GAH-PE in the reaction mixture exchanged into 5 mM $NaPO_4$, 50 mM MES, pH 7.
Figure 10:
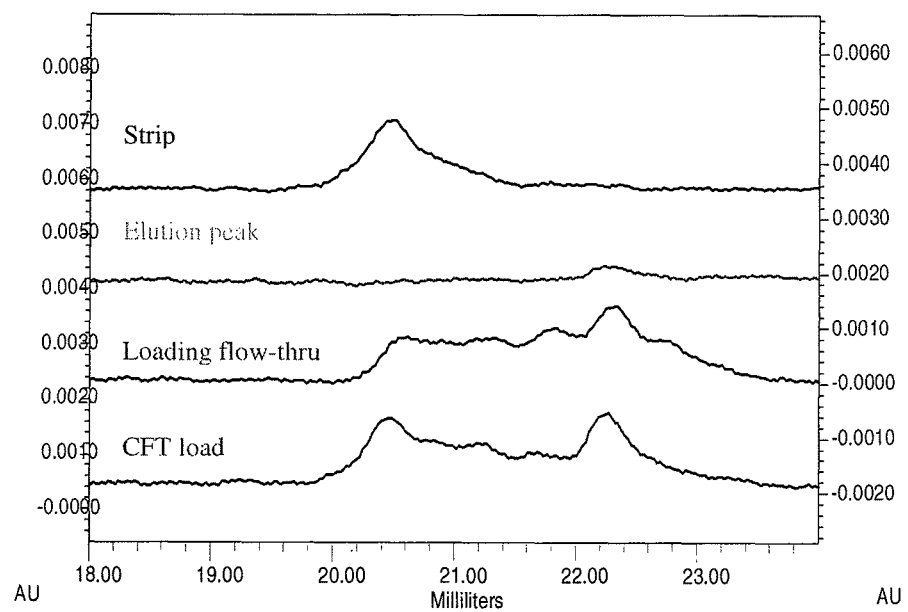
FIG. 10. HPSEC analysis of CFT samples in FIG. 9. Running buffer: 50 mM $NaPO_4$, 1 M NaCl, 2 M urea, pH 7.

To allow GAH-PE to flow through the column while retaining the GAH during the loading, the sodium phosphate concentration was increased. This led the experiment using 5 mM $NaPO_4$, 50 mM MES, pH 7 (FIG. 9). The chromatogram looks similar to that in FIG. 7 except that the elution peak is sharper. HPSEC analysis shows that both the GAH-PE and the GAH flow through the column during the loading and the strip contains GAH-PE with a purity of more than 75% and has no GAH (FIG. 10).

Figure 11:
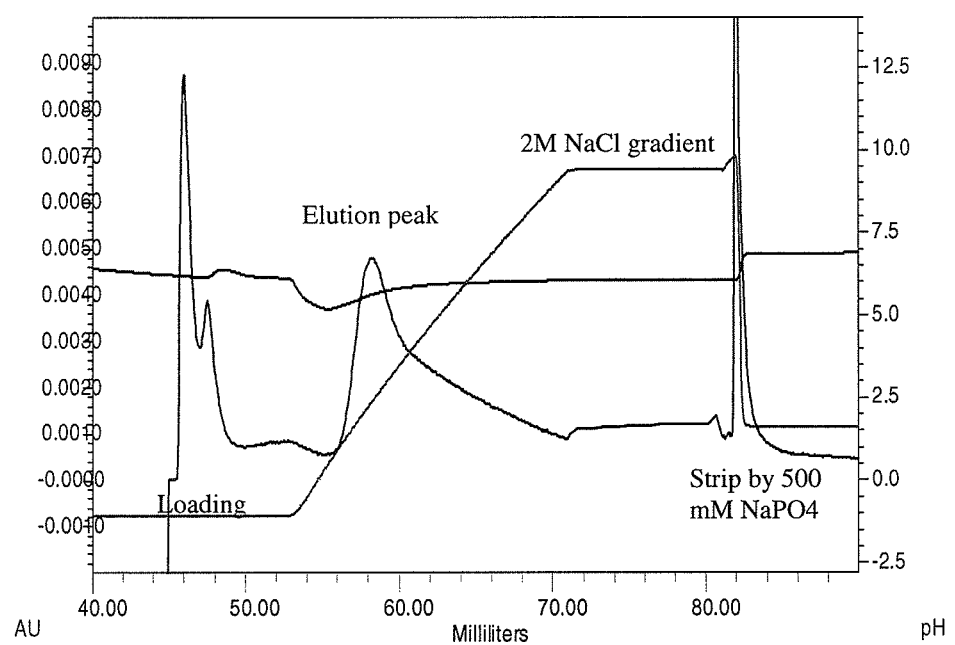
FIG. 11. CFT purification of the GAH-PE in the reaction mixture exchanged into 10 mM $NaPO_4$, pH 6.
Figure 12:
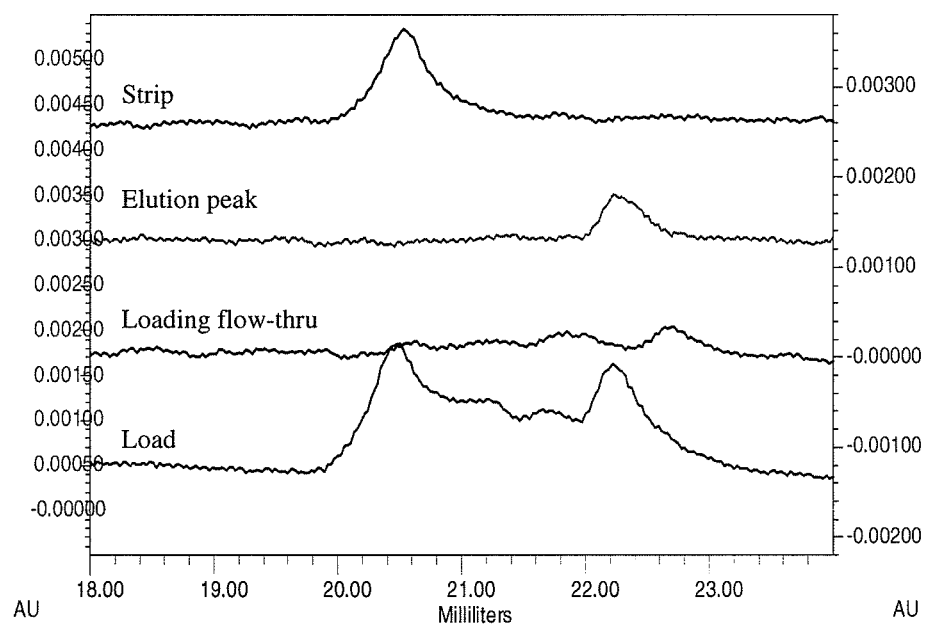
FIG. 12. HPSEC analysis of CFT samples in FIG. 11. Running buffer: 50 mM $NaPO_4$, 1 M NaCl, 2 M urea, pH 7.

Another experiment involved lowering the pH to 6 from 7 while keeping the sodium phosphate concentration at 10 mM. CFT is the only appropriate option due to the instability of CHT below pH 6.5, and work thus continued only with CFT. As shown in FIG. 11, the loading flow-through peak is much smaller than that in FIG. 9. A pH drop of 0.9 pH units occurs in the beginning of the NaCl gradient. The elution peak is much larger than that in FIG. 9. HPSEC analysis of the CFT samples indicates that the GAH-PE and the GAH are retained during the loading, the retained GAH and other contaminants are eluted during the NaCl gradient, and the GAH-PE remains bound to the column until stripped by 500 mM $NaPO_4$ and its purity in the strip is more than 95%.

Figure 13:
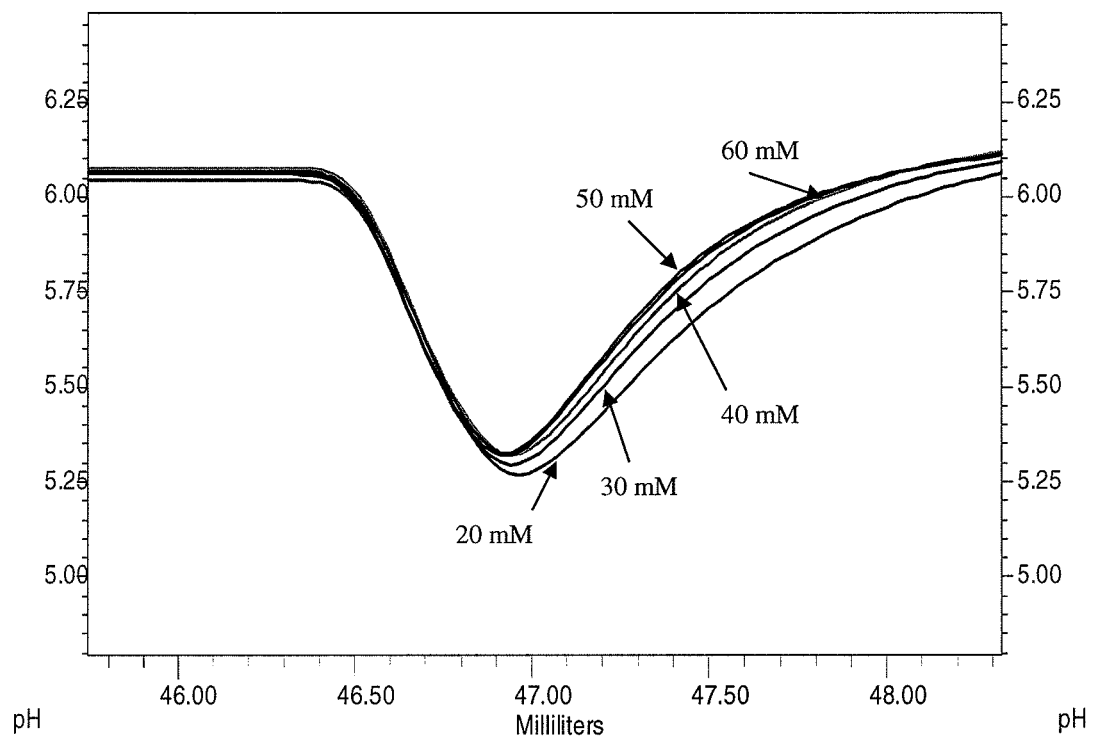
FIG. 13. Impact of the addition of MES in the wash solution on the pH drop during high-salt wash on CFT.

To simplify the process, the NaCl gradient was converted into a high-salt step wash to remove the retained GAH and other contaminants. In addition to 1 M NaCl, various concentrations of MES were added in the wash solution as a co-buffer with the 10 mM $NaPO_4$ aiming to minimize the pH drop that occurs when a high concentration of NaCl is applied to CFT. After a series of mock experiments using different wash solutions, their chromatograms were overlaid. It is shown in FIG. 13 that the pH drop is 0.77, 0.76, 0.76, 0.75, and 0.74 pH units in the presence of 20, 30, 40, 50, and 60 mM of MES, respectively. Compared to a pH drop of 0.9 pH units in the absence of MES (FIG. 11), MES helps mitigate the pH drop and its duration but its impact is not dramatic. There is almost no difference between 20 mM and 60 mM for the mitigation of the pH drop. However, it appears that the duration of the pH drop is greatly reduced when 40 mM or more of MES is added to the wash solution. Therefore, the high-salt wash solution was set at 10 mM $NaPO_4$, 40 mM MES, 1 M NaCl, pH 6.

The equilibration buffer was modified to 2 mM $NaPO_4$, 50 mM MES, pH 6 to ensure an effective capture of the GAH-PE. The elution buffer was 300 mM $NaPO_4$ instead of 500 mM $NaPO_4$. A stronger strip buffer of 800 mM $KPO_4$ was temporarily used to determine if there is any GAH-PE remained in the column after the elution. An additional wash with the equilibration buffer was inserted between the high-salt wash and the elution for better control over the NaCl concentration in the elution pool.

Figure 14:
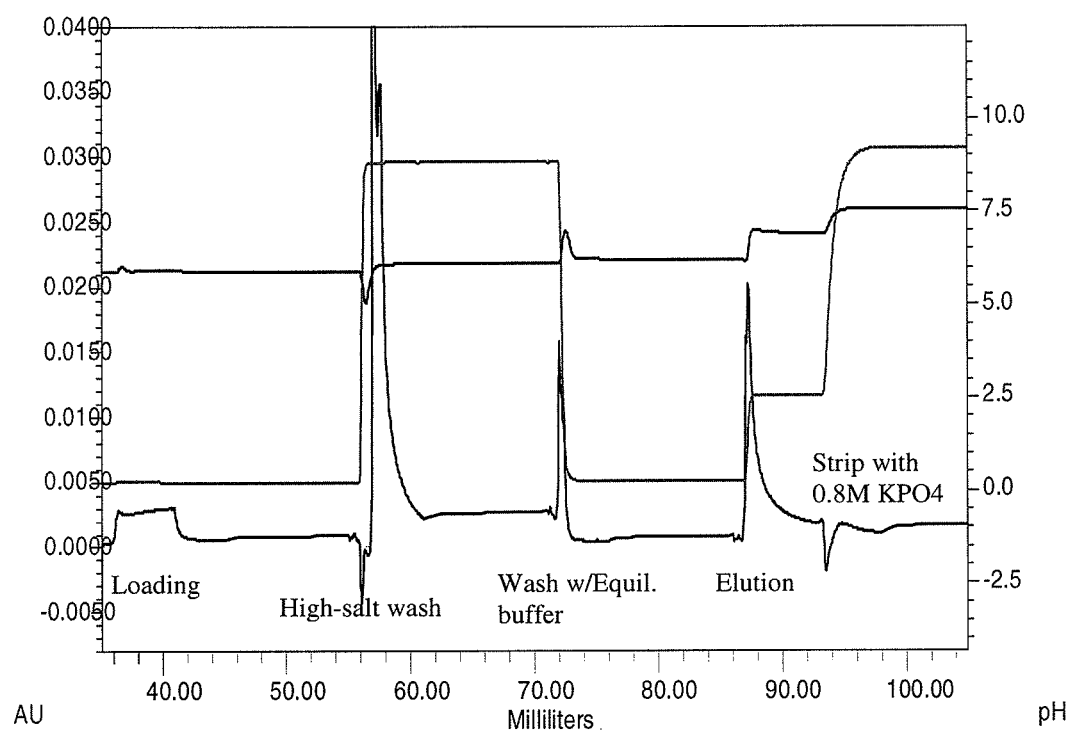
FIG. 14. CFT purification of the GAH-PE in the reaction mixture exchanged into 2 mM $NaPO_4$, 50 mM MES, pH 6.
Figure 15:
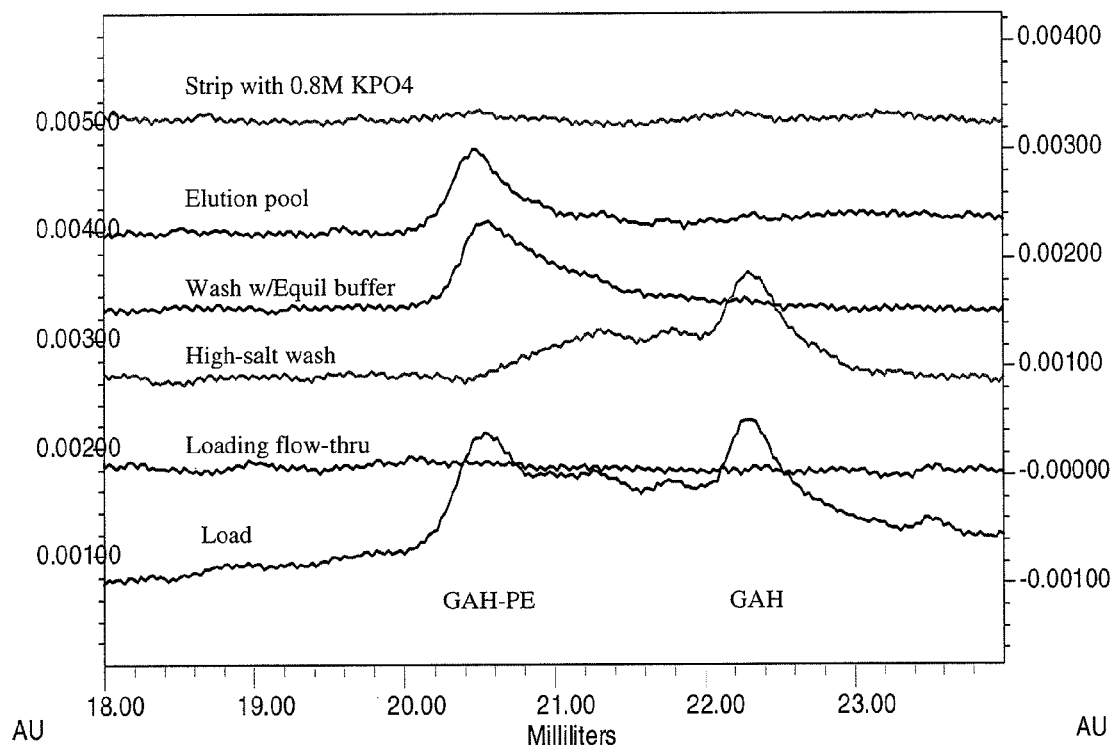
FIG. 15. HPSEC analysis of CFT samples in FIG. 14. Running buffer: 50 mM $NaPO_4$, 1 M NaCl, 2 M urea, pH 7.

A CFT run with the above modifications is presented in FIG. 14. As expected, the flow-through peak is small during the loading and a large peak appears during the high-salt wash. The tailing part of the high-salt wash peak does not fall back to the baseline indicating an insufficient wash. There is a small peak accompanying a pH jump from 6.1 to 7 during the wash with the equilibration buffer. This increase in pH is due to the decrease in NaCl concentration forcing protons from solution onto the surface of the CFT. The elution peak is surprisingly small compared to the high-salt wash peak. The strip peak with 0.8 M KPO4 was very small, which is a good indication for the effective elution of the GAH-PE by 300 mM $NaPO_4$. The results of HPSEC analysis of the CFT samples are shown in FIG. 15. The size of the GAH-PE peak in the load is close to that of the GAH peak, which suggests that, if the recovery of GAH-PE and GAH is equally well from CFT, the size of the elution peak should not be far off from that of the high-salt wash peak. No GAH-PE and GAH is found in the loading flow-through. Most of the GAH and the contaminants come out in the high-salt wash. Some of the retained GAH-PE is found in the wash with equilibration buffer. The pH jump to 7 from 6.1 upon the decreasing NaCl concentration elutes some of the GAH-PE. The purity of the GAH-PE in the elution pool is more than 95%. The strip by 0.8 M $KPO_4$ confirms that there is little GAH-PE left in the column after the elution by 300 mM $NaPO_4$.

Some modifications on the CFT operation were made based on the above observations. The duration of the high-salt wash was extended and the wash with equilibration buffer eliminated. The original strip buffer of 500 mM $NaPO_4$ will replace the 0.8 M KPO4. The new CFT chromatography method was as follows:

Pre-equilibration: 5 column volumes of 500 mM $NaPO_4$, pH 6.5 at 300 cm/hr

Equilibration: 5 column volumes of 2 mM $NaPO_4$, 50 mM MES, pH 6

Figure 16:
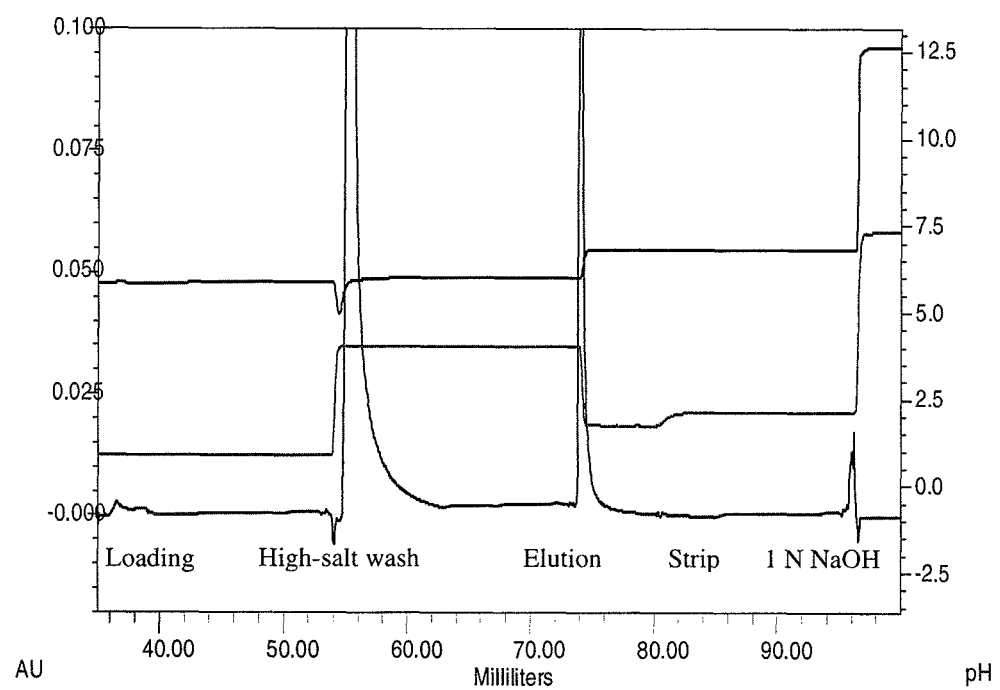
FIG. 16. The updated CFT purification of the GAH-PE in the reaction mixture exchanged into 2 mM $NaPO_4$, 50 mM MES, pH 6.
Figure 17:
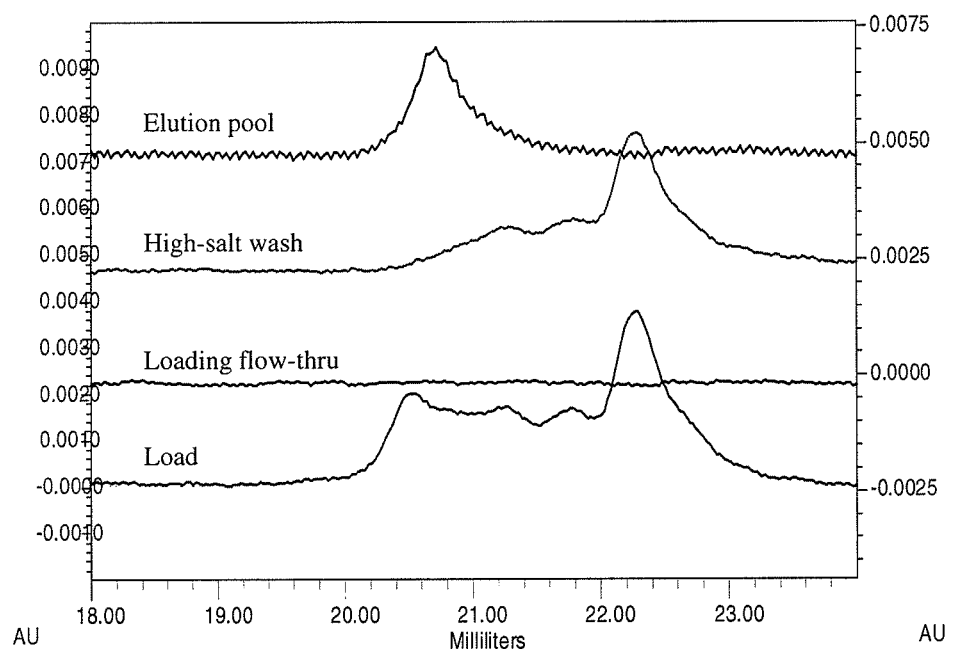
FIG. 17. HPSEC analysis of CFT samples in FIG. 16. Running buffer: 50 mM $NaPO_4$, 1 M NaCl, 2 M urea, pH 7.
Figure 18:
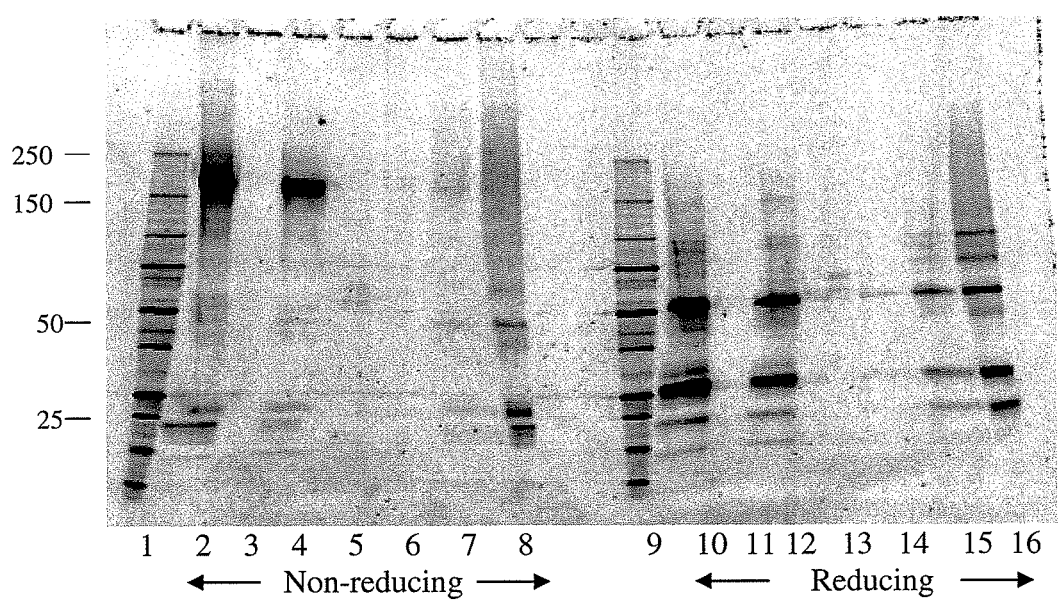
FIG. 18. SDS-PAGE with Flamingo staining of CFT samples. Lane 1: Molecular weight markers; Lane 2: CFT load; Lane 3: Loading flow-through; Lane 4: High-salt wash; Lane 5: Strip; Lane 6: Sanitization by 1 N NaOH; Lane 7: Elution pool; Lane 8: Purified GAH-PE std; Lane 9: Molecular weight markers; Lane 10: CFT load; Lane 11: Loading flow-through; Lane 12: High-salt wash; Lane 13: Strip; Lane 14: Sanitization by 1 N NaOH; Lane 15: Elution pool; Lane 16: Purified GAH-PE std.

Loading: approximately 0.5 mg of GAH-PE conjugates in the conjugation reaction mixture that is exchanged into the equilibration buffer beforehand (note: loading is not optimized yet).
Wash: 10 column volumes of 10 mM NaPO$_4$, 40 mM MES, 1 M NaCl, pH 6
Elution: 6 column volumes of 300 mM NaPO$_4$, pH 6.5
Strip: 5 column volumes of 500 mM NaPO$_4$, pH 6.5
Sanitization: 5 column volumes of 1 N NaOH
Storage: 5 column volumes of 0.1 N NaOH The chromatogram of an updated CFT run is shown in FIG. 16. The results of HPSEC analysis of the CFT samples is shown in FIG. 17. All results are as expected except that the content of the GAH-PE in the load is much lower than those in the previous runs. A possible reason is that an additional centrifugation of the GAH-PE conjugation reaction mixture before the buffer exchange removes some precipitated GAH-PE conjugates. The purity of the GAH-PE in the elution pool is more than 95%. The SDS-PAGE analysis of the CFT samples is shown in FIG. 18. It is confirmed from Lane 3 and 11 that there is no GAH-PE in the loading flow-through. Lane 4 (high-salt wash) shows that there is a large dark band near 150 kd, the typical molecular weight of IgG. Unlike in Lane 2 (CFT load), there are only a few very faint bands above 150 kd in Lane 4 even though the sample is heavily loaded. This indicates that the high-salt wash removes the GAH but has little impact on the GAH-PE. No meaningful detection of the GAH-PE in Lane 5 (strip) and 6 (1 N NaOH) indicates a good recovery of GAH-PE from the column. The profile of the elution pool is very comparable to that of the purified GAH-PE standard under the non-reducing condition (Lane 7 and 8) and the reducing condition (Lane 15 and 16).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of purifying an antibody-agent conjugate from unconjugated antibody and unconjugated agent, wherein the antibody is an IgG and the agent comprises phycoerythrin, the method comprising, (a) contacting a mixture of conjugate, unconjugated antibody, and unconjugated agent to a mixed mode chromatography support under conditions to allow binding of the conjugate, unconjugated antibody, and unconjugated agent to the support;

(b) contacting the support with a buffer, the contacting comprising an increased concentration of salt such that the unconjugated antibody and unconjugated agent are substantially removed from the support while at least a majority of the conjugate remains bound to the support; and then (c) eluting the conjugate from the support, wherein the eluting comprises increasing the concentration of the buffer, thereby purifying the antibody-agent conjugate from unconjugated antibody and unconjugated agent.

2. The method of claim 1, wherein the concentration of salt in step (b) is between 0.5 and 4M.

3. The method of claim 2, wherein the salt is NaCl.

4. The method of claim 1, wherein step (c) comprises reducing the salt concentration compared to the salt concentration step (b).

5. The method of claim 1, wherein the pH of the mixture in step (a) is between about pH 5.5 and pH 11.

6. The method of claim 1, wherein the pH of the buffer in step (b) is between about pH 5.5. and pH 11.

7. The method of claim 1, wherein the eluting step comprises contacting the support with an elution buffer having a pH between about pH 5.5. and pH 11.

8. The method of claim 1, wherein the buffer is a phosphate buffer.

9. The method of claim 1, wherein the mixed mode support comprises ceramic hydroxyapatite (CHT) or ceramic fluorapatite (CFT).

10. The method of claim 9, wherein the CHT is selected from the group consisting of hydroxyapatite CHT Type I, 20 micron; hydroxyapatite CHT Type I, 40 micron; hydroxyapatite CHT Type I, 80 micron; hydroxyapatite CHT Type II, 20 micron;
hydroxyapatite CHT Type II, 40 micron, and hydroxyapatite CHT Type II, 80 micron.

11. The method of claim 9, wherein the CFT is selected from the group consisting of CFT Type I, 40 micron and CFT Type II, 40 micron.

* * * * *